United States Patent [19]

Weiss et al.

[11] 3,984,451

[45] Oct. 5, 1976

[54] METHOD FOR PREPARING HYDRAZO-BIS-ACETONITRILES

[75] Inventors: Francis Weiss, Pierre Benite; Jean-Pierre Schirmann, Brignais, both of France

[73] Assignee: Produits Chimiques Ugine Kuhlmann, Paris, France

[22] Filed: May 21, 1975

[21] Appl. No.: 579,548

Related U.S. Application Data

[63] Continuation of Ser. No. 265,748, June 23, 1972, abandoned.

[52] U.S. Cl. ........................ 260/464; 260/239 AA; 260/465 E; 260/465.5 R; 260/566 B; 260/586 P
[51] Int. Cl.² ........................................ C07C 120/00
[58] Field of Search .............. 260/465.5 R, 465 E, 260/464, 566 B

[56] References Cited
UNITED STATES PATENTS

| | | | |
|---|---|---|---|
| 2,469,358 | 5/1949 | Alderson, Jr. et al. | 260/465.5 R |
| 2,770,643 | 11/1956 | Anderson | 260/566 B UX |
| 2,870,206 | 1/1959 | Meyer et al. | 260/566 B |

*Primary Examiner*—Joseph Paul Brust
*Attorney, Agent, or Firm*—Pennie & Edmonds

[57] ABSTRACT

This invention relates to a method for preparing hydrazo-bis-acetonitriles of the general formula:

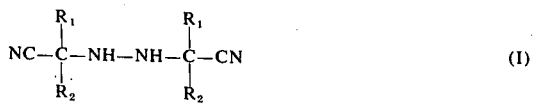

wherein $R_1$ and $R_2$ have the same meaning hereinafter given, which comprises:

a. i. reacting a carbonyl compound of the general formula:

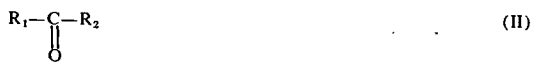

wherein $R_1$ and $R_2$ have the same meaning hereinafter given, with ammonia and hydrogen peroxide in the presence of cyanogen or a nitrile of the formula $$R_3(CN)_n \qquad (III)$$

wherein $n$ is an integer from 1 to 6 and $R_3$ is an unsubstituted or substituted saturated aliphatic, acyclic or cyclic radical of from 1 to 12 carbon atoms or a benzenyl or pyridinyl radical, to form a symmetrical azine of the formula

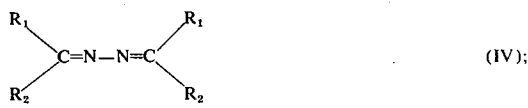

ii. oxidizing a secondary alcohol of

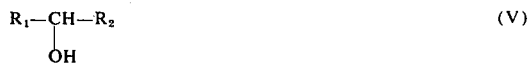

wherein $R_1$ and $R_2$ have the same meaning hereinafter given, at a temperature and pressure which is sufficient to maintain the alcohol in the liquid phase and result in a liquid phase mixture containing the peroxidic products of the auto-oxidation of the alcohol [v] and reacting auto-oxidation products with ammonia and cyanogen or the nitrile $R_3(CN)_n$ of formula (III) to form the symmetrical azine of formula (IV)

b. eliminating unreacted ammonia from the medium resulting from (a);

c. reacting the azine of formula (IV) contained in the ammonia-free medium resulting from (b) with at least two moles of hydrocyanic acid per mole of azine; and d. recovering the hydrazo-bis-acetonitrile of formula (I).

25 Claims, No Drawings

METHOD FOR PREPARING HYDRAZO-BIS-ACETONITRILES

This is a continuation of application Ser. No. 265,748, filed June 23, 1972, now abandoned.

BACKGROUND OF THE INVENTION

I. Field of the Invention

This invention relates to the preparation of nitriles and specifically to the preparation of hydrazo-bis-acetonitriles by the method of reacting an azine with hydrocyanic acid.

II. Description of the Prior Art

Hydrazo-bis-acetonitriles can be obtained by the known method of reacting an aldehyde or ketone with hydrazine and an alkaline cyanide in the presence of an acid (for example, Thiele and Heuser, Ann., 290 p. 1-40 (1896)). In a variation of this method, the aldehyde or ketone is first reacted with hydrazine thereby forming an azine and the azine is then reacted with hydro cyanic acid to form the hydrazo-bis-acetonitrile (for example, U.S. Pat. No. 2,469,358). In both methods, pure reactants are employed and each method requires the use of hydrazine, which is an expensive reactant.

One method for preparing azines comprises the oxidation of ammonia in the presence of a ketone or aldehyde by means of an oxidizing medium comprising hydrogen peroxide and cyanogen or a nitrile. This method is fully disclosed in commonly assigned pending U.S. application Ser. No. 152,413, filed June 11, 1971, now abandoned, which is incorporated by reference herein.

Another method for preparing azines comprises oxidizing a secondary alcohol in the liquid phase to form peroxide products of the auto-oxidation of the alcohol and subsequently reacting the peroxidic products with ammonia in the presence of cyanogen or a nitrile. This method is fully disclosed in commonly assigned pending U.S. application Ser. No. 230,038, filed Feb. 28, 1972, now abandoned, which is also incorporated by reference herein.

The azines prepared according to each of these methods are formed in complex reaction media which in addition to unreacted products, can also contain solvent and a carboxylic amide resulting from the transformation of the nitrile during the oxidation reaction.

SUMMARY OF THE INVENTION

It has been surprisingly discovered that the hydrazo-bis-acetonitriles of this invention can be conveniently and economically prepared in increased yields without resorting to purification of the azine reactants. The method of this invention employs the crude reaction mixtures obtained from the aforementioned processes for preparing azines.

Broadly, the method of this invention is one for preparing hydrazo-bis-acetonitriles of the general formula:

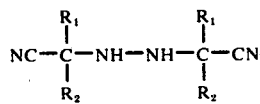

(I)

wherein $R_1$ is hydrogen and $R_2$ or $R_1$ and $R_2$ each is a straight or branched chain alkyl radical or cycloalkyl radical of up to 12 carbon atoms, a hydrocarbon radical of from 6 to 12 carbon atoms containing a benzene nucleus or $R_1$ and $R_2$ of both the

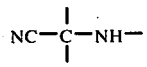

moieties together form a straight or branched chain alkylene radical being unsubstituted or substituted with one or more chloro, bromo or fluoro atoms or nitro or methoxy groups, which comprises:

a. i. reacting a carbonyl compound of the general formula:

(II)

wherein $R_1$ is hydrogen and $R_2$ or $R_1$ and $R_2$ each is a straight or branched chain alkyl radical or cycloalkyl radical of up to 12 carbon atoms, a hydrocarbon radical of from 6 to 12 carbon atoms containing a benzene nucleus or $R_1$ and $R_2$ together from a straight or branched chain alkylene radical being unsubstituted or substituted with one or more chloro, bromo or fluoro atoms or nitro or methoxy groups, with ammonia and hydrogen peroxide in the presence of cyanogen or a nitrile of the formula $$R_3(CN)_n \quad \text{(III)}$$

wherein $n$ is an integer from 1 to 6 and $R_3$ is an unsubstituted or substituted saturated aliphatic, acyclic or cyclic radical of from 1 to 12 carbon atoms or a benzenyl or pyridinyl radical, to form a symmetrical azine of the formula:

(IV);

or ii. oxidizing a secondary alcohol of the general formula:

(V)

wherein $R_1$ and $R_2$ each is a straight or branched chain alkyl radical or cycloalkyl radical of up to 12 carbon atoms, a hydrocarbon radical of from 6 to 12 carbon atoms containing a benzene nucleus or $R_1$ or $R_2$ together form a straight or branched chain alkylene radical being unsubstituted or substituted with one or more chloro, bromo or fluoro atoms or nitro or methoxy groups, with molecular oxygen or a gaseous mixture containing the same, at a temperature and pressure which is sufficient to maintain the alcohol in the liquid phase and result in a liquid phase mixture containing the peroxidic products of the auto-oxidation of the alcohol and reacting the auto-oxidation products with ammonia and cyanogen or the nitrile

of formula (III) to form the symmetrical azine of formula (IV);

b. eliminating unreacted ammonia from the medium resulting from (a);
c. reacting the azine of formula (IV) containing in the ammonia-free medium resulting from (b) with at least two moles of hydrocyanic acid per mole of azine; and
d. recovering the hydrazo-bis-acetonitrile of formula (I).

DESCRIPTION OF THE PREFERRED EMBODIMENTS

The method of this invention employs azines which can be prepared by the method disclosed in Ser. No. 152,413 filed June 11, 1971 or Ser. No. 230,038 filed Feb. 28, 1972.

In the method of Ser. No. 152,413, a carbonyl compound

is reacted with cyanogen or a nitrile of the formula

to form the azine (IV).

When $R_1$ of the carbonyl compound (II) is hydrogen, the carbonyl compound is an aldehyde and the resulting azine (IV) is an aldazine (VI). Reacting the aldazine with hydrocyanic acid according to the method of this invention results in a hydrazo-bis-acetonitrile of the formula

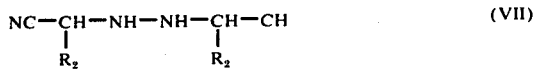

When $R_1$ of the carbonyl compound (II) is other than hydrogen, the carbonyl compound is a ketone and the resulting azine (IV) is a ketazine (VIII). Reacting the ketazine with hydrocyanic acid according to the method of this invention results in a hydrazo-bis-acetonitrile of formula (I) wherein $R_1$ is other than hydrogen.

Some examples of ketones conforming to formula (II) which are advantageously employed in the process include acetone, 2-butanone, 2-pentanone, 3-pentanone, methylisopropyl-ketone, methylisobutylketone, methylcyclohexylketone, acetophenone, benzophenone, cyclobutanone, cyclopentanone, cyclohexanone, 2-methylcyclohexanone, 4-methylcyclohexanone, 2,4-dimethyl cyclohexanone, 3,3,5-trimethylcyclohexanone, cycloheptanone, cyclooctanone, cyclodecanone and cyclododecanone.

Some examples of aldehydes of formula (II) which are advantageously employed in the above process include acetaldehyde, propionaldehyde, butyraldehyde, isobutyraldehyde, valeric aldehyde, pivalaldehyde, oenanthal, hexahydrobenzaldehyde, p-nitrobenzaldehyde and β-methoxypropionaldehyde.

The nitriles conforming to formula (III) which can be advantageously employed in the process include the mononitriles and polynitriles wherein the radical $R_3$ is a hydrocarbon radical containing up to 12 carbon atoms, which hydrocarbon radical can be a cyclic or acyclic radical or an aromatic radical such as a benzenyl or pyridinyl radical. Moreover the radical $R_3$ can contain substituents advantageously selected from among those groups which are not susceptible to oxidation under the conditions of the reaction, as for example, amide, carboxylic, carboxylic ester, nitro, fluoro, chloro, bromo, iodo, hydroxy, oxy ether, acetal, epoxy, sulfoxide, sulfur, sulfone and sulphonic acid groups.

In addition to cyanogen, specific examples of formula (III) nitriles which are advantageously employed include acetonitrile, propionitrile, butyronitrile, isobutyronitrile, cyclohexylcarboxylic nitrile, benzonitrile, tolunitriles, the cyanopyridines, the mono- di- and trichloroacetonitriles, m-chlorobenzonitrile, p-methoxybenzonitrile, p-nitrobenzonitrile, m-trifluoromethylbenzonitrile, glycolonitrile, epsilon-hydroxycapronitrile, cyanoacetic acid, the amides and alkyl esters of cyanoacetic acid, the amide and alkyl esters of beta-cyanopropionic acid, malononitrile, succinonitrile, glutaronitrile, adiponitrile, pimelonitrile, suberonitrile, the phthalonitriles and the nitriles which are prepared from the cyanoethylation with acrylonitrile or methacrylonitrile of water, an alcohol, a polyol and a carboxylic acid.

Examples of nitriles prepared from cyanoethylation include beta-hydroxypropionitrile, β,β'-oxydipropionitrile, the β-alkoxypropionitriles such as β-methoxypropionitrile, the cyanoethylation products of ethyleneglycol, propyleneglycol, glycerol and sorbitol. Certain of these nitriles can be formed in situ depending upon the constituents of the reaction medium, most notably, water or alcohol, by the reaction of acrylonitrile or methacrylonitrile, thus permitting the use of these ethylenic nitriles as starting materials in the process.

An advantageous method for preparing the azines according to Ser. No. 152,413 comprises reacting the components of the reaction medium in an aqueous solution or in the presence of a solvent. The solvent is advantageously selected from among the mono alkanols having from one to four carbon atoms, for example, methanol, ethanol, n-propanol, isopropanol, n-butanol, sec-butanol, isobutanol and tert-butanol. The reaction temperature is advantageously between about 0° and about 100° C. The reaction can be carried out at about atmospheric pressure or at a pressure of up to about ten atmospheres of pressure if necessary to maintain the ammonia in the reaction medium.

The reactants can be employed in stoichiometric amounts but a molar lack or excess of one or several reagents can also be utilized. For example, from about 0.2 to about 5 moles of aldehyde or ketone and ammonia per mole of hydrogen peroxide can be employed. The quantity of nitrile which is advantageously employed can vary from about 1 to about 10 equivalents of nitrile per mole of hydrogen peroxide.

The reactants can be used in their commercially available form. For example, hydrogen peroxide can be used in aqueous solutions of 30–90% hydrogen peroxide by weight and ammonia can be used either in anhydrous form or in the usual aqueous solution.

The reactants can be introduced into the reactor either simultaneously or in random sequence at a rate which will permit effective control of the exothermic reaction. The carbonyl compounds can be reacted with hydrogen peroxide in the known manner and the resulting peroxides can then be reacted with ammonia in the presence of nitrile. Similarly, the carbonyl compounds can be reacted with ammonia before adding the hydrogen peroxide and nitrile. And finally, an aminoperoxide can be prepared in the known manner by the reaction of a carbonyl compound, ammonia and hydrogen peroxide and this aminoperoxide can then be reacted with a nitrile to yield an azine.

It is advantageous to add to the reaction medium a stabilizing agent for hydrogen peroxide, such as phosphoric acid, nitrilotriacetic acid, ethylenediaminotetraacetic acid or the sodium salts of the aforesaid acids, and as a catalyst, an effective amount of an ammonium salt or an alkaline metal salt, for example, a lithium, sodium or potassium salt of a mineral hydracid or oxyacid, or of an aliphatic or aromatic carboxylic acid or arylsulphonic acid having less than 20 carbon atoms, the anions of which are stable under the oxidizing conditions of the reaction medium.

Some of the useful ammonium salts or alkaline metal salts include the ammonium, lithium, sodium and potassium salts whose anion is a fluoride, chloride, sulphate, nitrate, phosphate, pyrophosphate, borate, carbonate, formate, acetate, propionate, butyrate, isobutyrate, hexanoate, octanoate, dodecanoate, stearate, oxalate, succinate, glutarate, adipate, benzoate, phthalate, methanesulphonate, ethanesulphonate, benzenesulphonate and p-toluenesuphonate. The quantity of salt used can vary from 0.01 to 2% by weight of the total reaction mixture. The salt can be formed in situ. For example, if it is desired to employ an ammonium salt, the salt may be formed in situ by adding an acid to the ammonia-containing reaction medium.

In the method of Ser. No. 230,038, a secondary alcohol of the formula

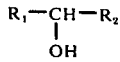

$$R_1-\underset{\underset{OH}{|}}{CH}-R_2 \quad (V)$$

is reacted with molecular oxygen or a gaseous mixture containing the same, at a temperature and pressure which is sufficient to maintain the alcohol in the liquid phase and result in a liquid phase mixture containing the peroxidic products of the auto-oxidation of the alcohol [V] and reacting the auto-oxidation products with ammonia, cyanogen or the nitrile

$$R_3(CN)_n \quad (III),$$

numerous examples of which are given above, to form a ketazine of formula (IV).

Some examples of secondary alcohols conforming to formula (V) which are advantageous in carrying out this method include isopropanol, 2-butanol, 2-pentanol, 3-pentanol, 3-methyl-2-butanol, 4-methyl-2-pentanol, 2-octanol, 1-cyclohexylethanol, 1-phenylethanol, diphenylcarbinol, cyclobutanol, cyclopentanol, cyclohexanol, 2-methylcyclohexanol, 3-methylcyclohexanol, 3,3,5-trimethylcyclohexanol, cycloheptanol, cyclooctanol and cyclododecanol.

As will be readily understood by one skilled in the art, many other secondary alcohols in addition to those specifically recited herein can be employed. Moreover the alcohol chosen can contain substituents which are stable in the reaction medium, as for example, methyl, methoxy, chloro, fluoro, or nitro groups.

In addition to producing a ketazine, the method can result in generally small quantities of derivatives of hydrazine and ketone, notably a diaziridine of the formula:

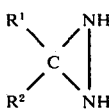

(IX)

and a hydrazone of the formula

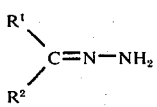

(X)

For the sake of simplicity, the method of Ser. No. 230,038 is referred to as one for preparing ketazines although it is to be understood that small quantities of the compounds of formulas (IX) and (X) can also be produced.

The auto-oxidation of the secondary alcohol or mixture of secondary alcohols can be carried out in known and conventional ways. The alcohol or mixture thereof is contacted with molecular oxygen or with a gas containing oxygen, as for example, air, under such conditions of pressure and temperature that the alcohol or mixture of alcohols as well as the peroxide compounds ketone(s) and hydrogen peroxide resulting from the auto-oxidation reaction will be in the liquid phase.

The temperature of the reaction can be maintained between about 60° and 180° C and advantageously between about 80° and 160° C. The reaction can be made to take place at atmospheric pressure if the nature of the starting materials and the temperature selected for the reaction permit. This reaction can also be made to take place at a pressure higher than the atmospheric pressure, for example, up to 50 atmospheres, if such pressure is necessary to maintain the reaction products in the liquid phase.

The reaction medium should be kept free of any heavy metal ions which risk catalyzing the decomposition of the peroxidic compounds. It is therefore advantageous to take such precautions to prevent the presence of these ions by the addition of agents to the reaction medium capable of sequestering the ions, for example, an alkaline phosphate, and by the use of inert materials for the construction of the oxidation reactor, for example, glass enamelled steel, stainless steel, and so forth.

It is known that the initiation of the oxidation reactions, using oxygen can be facilitated by the addition of substances to the reaction medium which give rise to free radicals, for example, the ketone peroxides, hydrogen peroxide, tertiobutyl peroxide and azobisisobutyronitrile. If desired, the aforesaid substances may be added to the secondary alcohol, for example, at a level of about 0.01 to 2% by weight.

The reaction can be carried out batch-wise or a continuous level of transformation can be employed; however, the latter is generally uneconomical. Similarly, while it is possible to reach the upper limit of transformation indicated above, it is known in this case that the selectivity of the reaction for the formation of peroxides is diminished and that there is a risk of attaining concentration of peroxides presenting the dangers of an explosion. The optimum level for the transformation should be selected bearing in mind the type of alcohol or alcohols employed and the operating conditions, factors which determine the stability of the peroxidic compounds.

While the peroxidic products can be concentrated by suitable means, as by removing the unreacted alcohol, it is advantageous for reasons of economy and safety to utilize the mixture resulting from the oxidation of secondary alcohol as in the following step of oxidizing with ammonia in the presence of a nitrile.

An advantageous manner of carrying out the second oxidizing step comprises mixing the crude product resulting from the first oxidizing step with ammonia and cyanogen or the nitrile (III) and carrying out the reaction at a temperature between about 0° and 100° C for a period of time which is sufficient to consume the greater part of the peroxidic oxygen present in the reaction medium.

The second oxidizing step can be carried out in the presence of water or a solvent in order to facilitate the homogenization of the mixture. The solvent can advantageously be an alkyl monoalcohol containing 1 to 4 carbon atoms, as for example, methanol, ethanol, n-propanol, isopropanol, n-butanol, sec-butanol, isobutanol and tert-butanol.

The quantity of ammonia employed can advantageously be between about 0.2 and 5 moles per equivalent of peroxidic oxygen. The nitrile can be employed at a level of from about 1 to 10 moles per equivalent of peroxidic oxygen. If desired, one can add a quantity of ketone in the form of the peroxide corresponding to the starting alcohol to the reaction medium to add to the quantity of ketone contained therein. This additional quantity of ketone can be added at a level of from 1 to 2 moles per equivalent of peroxidic oxygen.

The ammonia utilized can be anhydrous or in aqueous solution. In the case of the latter, it is advantageous to employ a 15% concentration of $NH_3$ by weight.

It is advantageous to add to the mixture of the peroxidic products from about 0.01 to 1% by weight of an agent which will stabilize the peroxides and hydrogen peroxide, as for example, phosphoric acid, nitrilotriacetic acid, ethylenediaminetetraacetic acid and the sodium salts of the aforesaid acids. It is also advantageous to add a catalyst such as an ammonium or alkaline metal salt, especially a lithium, sodium or potassium salt of a hydracid, mineral oxyacid, aromatic or aliphatic carboxylic acid or alkyl or arylsulfonic acid containing less than about 20 carbon atoms, and wherein the anions are stable under the oxidizing conditions of the reaction medium. Examples of such catalysts include the ammonium or alkaline metal salts whose anions are; fluoride, chloride, sulfate, nitrate, phosphate, pyrophosphate, borate, carbonate, formate, acetate, propionate, butyrate, isobutyrate, hexanoate, octanoate, dodecanoate, stearate, oxalate, succinate, glutarate, adipate, benzoate, phthalate, methanesulfonate, ethanesulfonate, benzene sulfonate, p-toluene-sulfonate and so forth. These salts can be employed as is or, in the case of the ammonium salts, the salt can be generated in situ by addition of the appropriate acid to the reaction medium containing ammonia. The quantity of salt employed is advantageously from about 0.01 to 2% by weight of the total reaction medium.

It is necessary according to the method of this invention to substantially eliminate the presence of ammonia which can be present in the crude azine produced by either of the above-described processes in order to avoid the formation of salts and polymers of hydrocyanic acid which could otherwise take place in an ammoniacal medium. This can be advantageously accomplished by evaporating the ammonia at atmospheric or reduced pressure or by neutralizing the ammonia with at least a stoichiometric amount of a mineral acid such as hydrochloric, phosphoric or sulfuric acid or a carboxylic acid such as formic or acetic acid.

It is advantageous to eliminate part or all of the unreacted aldehyde or ketone which can be present in the reaction medium of the method of Ser. No. 152,413 before adding the hydrocyanic acid in order to minimize the formation of the corresponding cyanohydrazine. This can readily accomplished by subjecting the reaction medium to fractional distillation.

The use of certain nitriles during the step of oxidizing the ammonia can result in a partial precipitation of carboxylic amide formed during the reaction. Filtration of this precipitate before the addition of the hydrocyanic acid is recommended.

Hydrocyanic acid is employed in the method of this invention at a level of at least two moles per mole of azine. Higher rates of conversion of the azine to the hydrazo-bis-acetonitrile have resulted from using an excess of hydrocyanic acid. The excess can be as high as 100% of the theoretically required amount.

The temperature of the reaction of azine and hydrocyanic acid can range from about 0° to about 100° C. The reaction generally lasts for several hours at the end of which the hydrazo-bis-acetonitrile precipitates in the crystalline state. If desired, the yield of crystalline precipitate can be increased by cooling the mixture to 0° C or less and/or diluting the medium with water prior to filtration.

The hydrazo-bis-acetonitriles are important intermediates for other syntheses, notably, for the preparation of the corresponding commercially useful azoic compounds.

The following examples illustrate the method of preparing hydrazo-bis-acetonitriles of this invention employing crude azines resulting from the reaction of an aldehyde or ketone and ammonia, hydrogen peroxide and a nitrile. In a manner similar to that of the examples, hydrazo-bis-acetonitriles can be prepared using crude azines resulting from the reaction of the peroxidic products of a secondary alcohol with ammonia and a nitrile.

EXAMPLE 1

A solution of 41 gm of acetonitrile (1.0 mole), 116 gm acetone (2 moles), 36 gm of water (2 moles), 2 gm of the disodium salt of ethylenediaminetetraacetic acid and 0.4 gm of ammonium acetate were placed in a reaction vessel. The temperature of the reaction medium was increased to 50° C and 4.6 gm of gaseous ammonia (0.27 moles) were bubbled into the medium, dissolving therein. 41 gm of a 67% aqueous solution of hydrogen peroxide (0.8 moles) were then added to the reaction medium over a period of two hours and ammonia was continuously bubbled into the medium at a rate of 5.2 gm/hour (0.3 moles/hour). The medium was left to react for six hours at the same temperature. At the end of the reaction, a sample of the mixture was analyzed. The amount of acetoneazine determined by chemical and gas phase chromatographic analysis was 62.8 gm (0.56 moles).

The reaction mixture was then subjected to distillation under reduced pressure (200 mm Hg.) until the temperature reached 50° C thereby eliminating the presence of the excess ammonia, acetone and acetonitrile. In this manner, 218 gm of an aqueous solution containing 56 gm acetoneazine (0.5 moles), 49.5 gm of acetamide and traces of ammonia, acetone and acetonitrile were recovered.

This solution of crude acetoneazine was placed in a mechanically agitated reactor of 750 cm³ equipped with a thermometer as well as a double walled dropping funnel and a condensor both of which were cooled to −10° C by the circulation of brine. 36 gm of liquid hydrocyanic acid (1.3 moles) were introduced into the dropping funnel. Thereafter the hydrocyanic acid was added drop-wise over a period of 1 hour to the reaction medium maintained at 15° C in the reactor. Precipitation of a solid crystalline material at a rate proportionate to the addition of hydrocyanic acid was observed. When precipitation had terminated, 125 cm³ of water were added to the reaction mixture which was then left to react for 3 hours at 15° C. The precipitate which had formed was filtered and washed with water. After the precipitate was drained and dried, 74.6 gm of hydrazo-bis-isobutyronitrile (freezing point = 87°–88° C) corresponding to a yield of 85% by comparison with the acetoneazine employed were recovered.

EXAMPLE 2

58.6 gm of acetonitrile (1.43 moles) in 460 gm methanol were placed in a reactor. The solution was heated to 40° C and over a period of one hour, 69.5 gm of a 70% aqueous solution of hydrogen peroxide (0.5 moles $H_2O_2$) and a mixture of 140 gm cyclohexanone (1.43 moles), an 18.8% solution of ammonia (1.43 moles), 46 gm of methanol and 1.4 gm of the disodioum salt of ethylenediaminetetraacetic acid (EDTA) were simultaneously added. The mixture was left to react for three hours. Gas phase chromatographic analysis indicated the presence of 96 gm cyclohexanoneazine (0.5 moles) in the reaction mixture.

The reaction mixture was subjection to distillation under a pressure of 200 mm Hg. until the boiling point reached 50°C thus assuring elimination of excess ammonia.

The residual liquid containing two layers was placed in a 500 ml reactor equipped with mechanical agitation, a dropping funnel and a reflux condensor both of which were cooled to −10° C by the circulation of brine. 34 gm of liquid hydrocyanic acid (1.25 moles) were introduced into the dropping funnel. Thereafter the hydrocyanic acid was added drop-wise to the reaction medium maintained between 15° and 20° C over a period of one hour. Precipitation of a solid crystalline material was observed. 125 cm³ of water were added to the mixture which was left to react further for three hours at 20° C. The precipitate thus obtained was filtered, washed with water and drained. After drying of the material, 121 gm hydrazo-bis-cyclohexyl-acetonitrile (freezing point 143°–145°) corresponding to a yield of 98% by comparison to the cyclohexanoneazine employed were recovered.

EXAMPLE 3

A solution of 410 gm acetonitrile (10 moles), 180 gm water, 10 gm of the disodium salt of ethylenediaminetetraacetic acid and 1.5 gm of ammonium acetate in 3200 gm methanol was added to a reactor. 230 gm of gaseous ammonia (13.5 moles) were bubbled into the medium dissolving therein. Thereafter 720 gm isobutyraldehyde (10 moles) and separately, 280 gm of a 61% aqueous solution of hydrogen peroxide (5 moles $H_2O_2$) were progressively added to the reaction medium. The medium was left to react for 48 hours at the same temperature. A sample of the medium was analyzed at the completion of the reaction. Chemical analysis showed the presence of 98 gm isobutyraldazine.

The unreacted ammonia, methanol and isobutyraldehyde were evaporated under 200 mm Hg. until the boiling temperature reached 50° C.

The residual liquid containing two layers was placed in a mechanically agitated reactor equipped with a thermometer as well as a dropping funnel and condensor, both of which were cooled to −10° C by a circulation of brine. The reaction medium was left to react for three hours. The upper organic layer was decanted and subjected to distillation under reduced pressure of 0.1 mm Hg. In this manner, 53 gm of hydrazo-bis-isopropyl acetonitrile (0.27) identified by infrared and mass spectrometry were recovered.

We claim:
1. A method for preparing hydrazo-bis-acetonitriles of the general formula

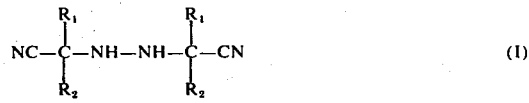

wherein $R_1$ is hydrogen and $R_2$ or $R_1$ and $R_2$ each is a straight chain alkyl radical of from 1 to 12 carbon atoms, a branched chain alkyl radical of from 3 to 12 carbon atoms, a cycloalkyl radical of from 3 to 12 carbon atoms or a phenyl radical or $R_1$ and $R_2$ together form a straight or branched chain alkylene radical of from 4 to 12 carbon atoms being unsubstituted or substituted with one or more chloro, bromo or fluoro atoms or nitro or methoxy groups, which consists essentially of:
a. reacting in a single reaction medium (i) a carbonyl compound of the general formula

wherein $R_1$ is hydrogen and $R_2$ or $R_1$ and $R_2$ each is a straight chain alkyl radical of from 1 to 12 carbon atoms, a branched chain alkyl radical of from 3 to 12 carbon atoms, a cycloalkyl radical of from 3 to 12 carbon atoms or a phenyl radical or $R_1$ and $R_2$ together form a straight or branched chain alkylene radical of from 4 to 12 carbon atoms being unsubstituted or substituted with one or more chloro, bromo or fluoro atoms or nitro or methoxy groups, (ii) ammonia, (iii) hydrogen peroxide, and (iv) cyanogen or a nitrile of the formula

wherein n is an integer from 1 to 6 and R₃ is a straight chain alkyl radical of from 1 to 12 carbon atoms, a branched chain alkyl radical of from 3 to 12 carbon atoms, a cycloalkyl radical of from 3 to 12 carbon atoms, a benzene or pyridine radical, said radical being unsubstituted or substituted with one or more halogen atoms or carbamyl, carboxylic, nitro, hydroxy, epoxy, or sulfonic acid groups, to form a symmetrical azine of the formula

b. eliminating unreacted ammonia from the medium resulting from (a) by evaporating unreacted ammonia at atmospheric or reduced pressure, or by neutralizing the unreacted ammonia with at least a stoichiometric amount of hydrochloric acid, phosphoric acid, sulfuric acid, formic acid or acetic acid;

c. reacting the ammonia-free medium resulting from (b) with at least two moles of hydrocyanic acid per mole of azine; and d. recovering the hydrazo-bis-acetonitrile of Formula (I).

2. The method of claim 1 wherein the carbonyl compound (II) is acetaldehyde, propionaldehyde, butyraldehyde, isobutyraldehyde, valerylaldehyde, pivalaldehyde, oenanthal, hexahydrobenzaldehyde, p-nitrobenzaldehyde or β-methoxy-propionaldehyde.

3. The method of claim 1 wherein the carbonyl compound (II) is acetone, 2-butanone, 2-pentanone, 3-pentanone, methylisopropylketone, methylisobutylketone, methylcyclohexylketone, acetophenone, benzophenone, cyclobutanone, cyclopentanone, cyclohexanone, 2-methylcyclohexanone, 4-methylcyclohexanone, 2,4-dimethylcyclohexanone, 3,3,5-trimethylcyclohexanone, cycloheptanone, cyclooctanone, cyclodecanone or cyclododecanone.

4. The method of claim 1 wherein the nitrile is added to the reaction medium of step (a).

5. The method of claim 1 wherein from about 0.2 to about 5 moles of carbonyl compound and ammonia per mole of hydrogen peroxide are reacted.

6. The method of claim 1 wherein from about 1 to about 10 molar equivalents of nitrile per mole of hydrogen peroxide are present in the reaction medium.

7. The method of claim 1 wherein from about 0.01 to 2% by weight of an ammonium or alkaline metal salt of a hydracid, mineral oxyacid, aromatic or aliphatic carboxylic acid or alkyl or arylsulfonic acid, all of the above having less than about 20 carbon atoms, and wherein the anions are stable under the oxidizing conditions of the reaction medium is added as a catalyst to the reaction medium of step (a).

8. The method of claim 1 wherein at least part of the unreacted carbonyl compound (II) present in the reaction medium is removed therefrom before carrying out step (c).

9. The method of claim 1 wherein hydrocyanic acid is used in excess up to about 100% of the theoretically required amount.

10. The method of claim 1 wherein the temperature of the reaction of step (c) is maintained between about 0° and 100° C.

11. The method of claim 1 wherein step (b) is carried out by neutralizing the unreacted ammonia with at least a stoichiometric amount of hydrochloric acid, phosphoric acid, sulfuric acid, formic acid or acetic acid.

12. The method of claim 1 wherein the nitrile (III) is acetonitrile, propionitrile, butyronitrile, isobutyronitrile, cyclohexylcarboxylic nitrile, benzonitrile, a tolunitrile, a cyanopyridine, mono-, di- or trichloroacetonitrile, m-chlorobenzonitrile, p-methoxybenzonitrile, p-nitrobenzonitrile, m-trifluoromethylbenzonitrile, glycolonitrile, epsilon-hydroxycapronitrile, cyanoacetic acid, an amide or alkyl ester of cyanoacetic acid, an amide or alkyl ester of beta-cyanopropionic acid, malononitrile, succinonitrile, glutaronitrile, adiponitrile, pimelonitrile, suberonitrile, a phthalonitrile, beta-hydroxypropionitrile, β,β'-oxydipropionitrile, a β-alkoxypropionitrile or a nitrile prepared from the cyanoethylation with acrylonitrile or methacrylonitrile of ethyleneglycol, propyleneglycol, glycerol, sorbitol or water.

13. The method of claim 12 wherein the nitrile prepared by cyanoethylation is formed in situ within the reaction medium of step (a).

14. A method for preparing hydrazo-bis-acetonitriles of the general formula

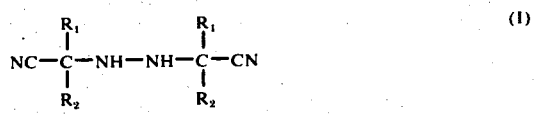

wherein R₁ is hydrogen and R₂ or R₁ and R₂ each is a straight chain alkyl radical of from 1 to 12 carbon atoms, a branched chain alkyl radical of from 3 to 12 carbon atoms, a cycloalkyl radical of from 3 to 12 carbon atoms or a phenyl radical or R₁ and R₂ together form a straight or branched chain alkylene radical of from 4 to 12 carbon atoms being unsubstituted or substituted with one or more chloro, bromo or fluoro atoms or nitro or methoxy groups, which consists essentially of:

a. oxidizing a secondary alcohol of the general formula

wherein R₁ and R₂ each is a straight chain alkyl radical of from 1 to 12 carbon atoms, a branched chain alkyl radical of from 3 to 12 carbon atoms, a cycloalkyl radical of from 3 to 12 carbon atoms or a phenyl radical or R₁ and R₂ together form a straight or branched chain alkylene radical of from 4 to 12 carbon atoms being unsubstituted or substituted with one or more chloro, bromo or fluoro atoms or nitro or methoxy groups, with molecular oxygen or a gaseous mixture consisting essentially of molecular oxygen, at a temperature and pressure which is sufficient to maintain the alcohol in the liquid phase to produce a mixture containing the peroxidic products of the auto-oxidation of the alcohol (V), said mixture being free of heavy metal ions, and reacting the auto-oxidation products with ammonia and cyanogen or a nitrile of the formula

wherein *n* is an integer from 1 to 6 and $R_3$ is a straight chain alkyl radical of from 1 to 12 carbon atoms, a branched chain alkyl radical of from 3 to 12 carbon atoms, a cycloalkyl radical of from 3 to 12 carbon atoms or a benzene or pyridine radical, said radical being unsubstituted or substituted with one or more halogen atoms or carbamyl, carboxylic, nitro, hydroxy, epoxy, or sulfonic acid groups, to form a symmetrical azine of the formula

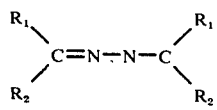 (IV);

b. eliminating unreacted ammonia from the medium resulting from (a) by evaporating unreacted ammonia at atmospheric or reduced pressure, or by neutralizing the unreacted ammonia with at least a stoichiometric amount of hydrochloric acid, phosphoric acid, sulfuric acid, formic acid or acetic acid;

c. reacting the ammonia-free medium resulting from (b) with at least two moles of hydrocyanic acid per mole of azine; and d. recovering the hydrazo-bis-acetonitrile of formula (I).

15. The method of claim 14 wherein the alcohol (V) is selected to be isopropanol, 2-butanol, 2-pentanol, 3-methyl-2-butanol, 4-methyl-2-pentanol, 2-octanol, 1-cyclohexylethanol, 1-phenylethanol, diphenylcarbinol, cyclobutanol, cyclopentanol, cyclohexanol, 2-methylcylohexanol, 3-methylcyclohexanol, 3,3,5-trimethylcyclohexanol, cycloheptanol, cyclooctanol or cyclododecanol.

16. The method of claim 14 wherein from about 0.01 to 2% by weight of a ketone peroxide, hydrogen peroxide, tertiobutyl peroxide of azobisisobutyronitrile is added to the reaction medium of step (a) to facilitate the oxidation of the alcohol (V).

17. The method of claim 14 wherein unreacted alcohol (V) is removed from the mixture of peroxidic products before reacting the latter with ammonia, cyanogen or nitrile (III).

18. The method of claim 14 wherein ammonia is utilized in step (a) at a level of from about 0.2 to 5 moles per equivalent of peroxidic oxygen.

19. The method of claim 14 wherein nitrile (III) is utilized in step (a) at a level of from about 1 to 10 moles per equivalent of peroxidic oxygen.

20. The method of claim 14 wherein the reaction of the auto-oxidation products of step (a) with ammonia, and cyanogen or nitrile (III) is maintained at a temperature between about 0° and 100° C.

21. The method of claim 14 wherein the nitrile (III) is acetonitrile, propionitrile, butyronitrile, isobutyronitrile, cyclohexylcarboxylic nitrile, benzonitrile, a tolunitrile, a cyanopyridine, mono-, di- or tri-chloroacetonitrile, m-chlorobenzonitrile, p-methoxybenzonitrile, p-nitrobenzonitrile, m-trifluoromethylbenzonitrile, glycolonitrile, epsilon-hydroxycapronitrile, cyanoacetic acid, an amide or alkyl ester of cyanoacetic acid, an amide or alkyl ester of beta-cyanopropionic acid, malononitrile, succinonitrile, glutaronitrile, adiponitrile, pimelonitrile, suberonitrile, a phthalonitrile, beta-hydroxypropionitrile, β,β'-oxydipropionitrile, a β-alkoxypropionitrile or a nitrile prepared from the cyanoethylation with acrylonitrile or methacrylonitrile of ethyleneglycol, propyleneglycol, glycerol, sorbitol or water.

22. The method of claim 14 wherein from about 0.01 to 2% by weight of an ammonium or alkaline metal salt of a hydracid, mineral oxyacid, aromatic or aliphatic carboxylic acid or alkyl or arylsulfonic acid containing less than about 20 carbon atoms and wherein the anions are stable under the oxidizing conditions of the reaction medium is added as a catalyst to the reaction medium of step (a).

23. The method of claim 14 wherein step (b) is carried out by neutralizing the unreacted ammonia with at least a stoichiometric amount of hydrochloric acid, phosphoric acid, sulfuric acid, formic acid or acetic acid.

24. The method of claim 14 wherein hydrocyanic acid is used in excess up to about 100% of the theoretically required amount.

25. The method of claim 14 wherein the temperature of the reaction of step (c) is maintained between about 0° and 100° C.

* * * * *